United States Patent
Park et al.

(10) Patent No.: US 8,610,565 B2
(45) Date of Patent: Dec. 17, 2013

(54) RFID TAG WITH LED AND RF IDENTIFICATION MANAGING METHOD USING THE SAME

(75) Inventors: Ji-Man Park, Daejeon (KR); Sung-Ik Jun, Daejeon (KR)

(73) Assignee: Electronics and Telecommunications Research Institute, Daejeon (KR)

(*) Notice: Subject to any disclaimer, the term of this patent is extended or adjusted under 35 U.S.C. 154(b) by 730 days.

(21) Appl. No.: 12/443,443

(22) PCT Filed: Jul. 18, 2007

(86) PCT No.: PCT/KR2007/003468
§ 371 (c)(1),
(2), (4) Date: Feb. 8, 2010

(87) PCT Pub. No.: WO2008/038896
PCT Pub. Date: Apr. 3, 2008

(65) Prior Publication Data
US 2010/0171586 A1    Jul. 8, 2010

(30) Foreign Application Priority Data
Sep. 28, 2006 (KR) .................. 10-2006-0095007

(51) Int. Cl.
*G08B 1/08* (2006.01)
(52) U.S. Cl.
USPC .............. 340/539.26; 340/5.1; 340/10.41
(58) Field of Classification Search
USPC ......... 340/825.53, 856.3, 539.26, 568.2, 643, 340/3.31
See application file for complete search history.

(56) References Cited

U.S. PATENT DOCUMENTS

| | | | | |
|---|---|---|---|---|
| 6,806,808 B1* | 10/2004 | Watters et al. | ............. | 340/10.41 |
| 7,649,455 B2* | 1/2010 | Easley et al. | ............. | 340/539.13 |
| 2004/0113790 A1* | 6/2004 | Hamel et al. | ............... | 340/572.1 |
| 2005/0001724 A1 | 1/2005 | Heinrich et al. | ........ | G08B 13/14 |
| 2005/0151616 A1 | 7/2005 | Nakazawa | ............... | H04B 1/00 |
| 2005/0151617 A1* | 7/2005 | Nakazawa | ..................... | 340/5.8 |
| 2006/0002109 A1* | 1/2006 | Imade | ........................ | 362/231 |
| 2006/0232417 A1* | 10/2006 | August et al. | ............. | 340/572.7 |

FOREIGN PATENT DOCUMENTS

| | | |
|---|---|---|
| EP | 1047015 | 10/2000 |
| JP | 2005-178964 | 7/2005 |
| KR | 2001-0006991 | 1/2001 |
| KR | 10-2005-0007719 | 1/2005 |
| KR | 10-2005-0031383 | 4/2005 |
| KR | 10-2005-0031384 | 4/2005 |

(Continued)

OTHER PUBLICATIONS

International Search Report mailed Oct. 23, 2007 for PCT/KR2007/003468.

*Primary Examiner* — Brian Zimmerman
*Assistant Examiner* — Omer S Khan
(74) *Attorney, Agent, or Firm* — Lowe Hauptman & Ham LLP

(57) ABSTRACT

A RFID tag having a LED is provided. The RFID tag includes an antenna, a RF processor, a controller, a memory, at least one of LEDs, and a LED switching unit. The RF processor receives and transmits a wireless signal through the antenna, and modulates and demodulates transmitted and received signal and data. The controller analyzes a received data outputted from the RF signal processor and generally controls the RFID tag. The memory stores the received data in response to the controller. The LED switching unit turns on/off at least one of the LEDs in response to the controller.

4 Claims, 12 Drawing Sheets

(56) References Cited

FOREIGN PATENT DOCUMENTS

| KR | 10-2005-0054421 | 6/2005 |
| KR | 10-2005-0066037 | 6/2005 |
| KR | 10-2005-0092259 | 9/2005 |
| KR | 10-2006-0088481 | 8/2006 |
| WO | 2005/064579 | 7/2005 |

\* cited by examiner (a)

(b)

RFID TAG WITH LED AND RF IDENTIFICATION MANAGING METHOD USING THE SAME

CROSS REFERENCE TO RELATED APPLICATION

This application claims the priority of Korean Patent Application No. 10-2006-0095007, filed on Sep. 28, 2006 in the KIPO (Korean Intellectual Property Office), the disclosure of which is incorporated herein in their entirety by reference. Further, this application is the National Phase application of International Application No. PCT/KR2007/003468, filed Jul. 18, 2007, which designates the United States and was published in English. Each of these applications is hereby incorporated by reference in their entirety into the present application.

TECHNICAL FIELD

The present invention relates a radio frequency identification (RFID) tag with a light emitting diode (LED) for selectively managing a large quantity of products or a plurality of patients in medical environment, distribution, or living environment.

BACKGROUND ART

In medical management environment for managing blood, medical supplies, and patients, the patients are managed by recoding information about patients at a register, or blood and medical supplies are managed by attaching barcodes having basic information such as a preservation period and identification.

Such a conventional management method using a barcode can resolve inconvenience to manually write down the information of management subjects to a related register. However, since it requires a barcode reader to contact a corresponding barcode to read information thereof, a manager needs to physically move to management subjects to read information and to identify the management subjects.

Especially, since the contamination and the miss-identification of blood or medical supplies are directly related to the life of patient, management subjects with a preservation period expired, and contaminated management subject must be accurately discriminated from others. Such an identifying operation generally takes lots of efforts and a long processing time. Furthermore, when harmful samples, contaminated samples, and samples of a corresponding patient are manually identified, errors are frequently made in general. Such a management error lets the contaminated blood, environmentally sensitive medical supplies, and medical supplies with a preservation data expired to be used for other people, thereby injuring other people.

In case of managing agricultural and marine products, agricultural and marine products may become rotten and decomposed easily due to management failure. In this case, the rotten and decomposed products must be identified and processed, manually. As described above, it requires lots of efforts and takes a long processing time. Also, it may give serious problems physically and economically due to inaccurate management.

In order to overcome the shortcoming of the conventional management method using a barcode and to effectively manage products, a radio frequency identification (RFID) was introduced. The RFID allows to recognize management subjects in non-contact manner regardless of characteristics of surface or material of management subjects and environmental variation, and to exchange data related to management subject because the RFID includes a micro chip. Such a RFID was embodied as a tag to be attached to all types of subjects including human and includes a micro chip and a wireless transceiving function. The RFID is generally called as a RFID tag. The RFID tag includes unique information and allows a reader to read the stored information through a wireless link. The RFID tag was introduced to manage information about a manufacturing process, a distribution process, a storage process, and a consuming process through wireless link by cooperating with an information system connected through a satellite, a mobile communication network, and the Internet.

As described above, the conventional RFID tag simply stores information about management subjects, and manages the management subjects by reading the information thereof through a reader. However, it is impossible to easily and effectively detect decomposed blood, contaminated medical supplies, and rotten agricultural and marine products using the conventional RFID tag. That is, it is very difficult to easily and accurately detect management subjects having a predetermined condition from a large quantity of management subjects.

DISCLOSURE OF INVENTION

Technical Problem

An aspect of the present invention is to provide a radio frequency identification (RFID) tag with a light emitting diode (LED) and a wireless recognition and management method using the same for quickly and accurately identifying management subjects having a predetermined condition from a large quantity of management subjects, and for quickly classifying and managing blood, medical supplies, agricultural and marine products according to contamination and decomposition levels for managing.

Technical Solution

According to an aspect of the invention, the invention provides a RFID (radio frequency identification) tag including: an antenna; a RF (radio frequency) processor for receiving and transmitting a wireless signal through the antenna, and modulating and demodulating transmitted and received signal and data; a controller for analyzing a received data outputted from the RF signal processor and generally controlling the RFID tag; a memory for storing the received data in response to the controller; at least one of LEDs (light emitting diode) for being turned on and off; and a LED switching unit for turning on/off at least one of the LEDs in response to the controller.

The RFID tag may further includes: at least one of sensors for detecting states of management subjects and various of peripheral environment; and a sensing signal processing unit for transforming a sensing signal outputted from at least one of the sensors to a digital value to be processable in the controller, and providing the digital value to the controller.

According to another aspect of the invention, the invention provides a wireless recognition and management method using a RFD (radio frequency identification) tag having a LED (light emitting diode), including: transmitting an issuing request signal to the RFID tag through a reader; transmitting data having management information about a subject where a corresponding RFID tag is attached to when a response for the issuing request signal is received from a RFD tag, requesting the RFID tag to store the data, and receiving a response thereof; and transmitting a predetermined condition to the RFID tag storing the data when a subject having the predetermined condition is required to identify, requesting the RFID tag to compare and control a LED of the RFID tag according to the condition.

According to yet another aspect of the invention, the invention provides a wireless recognition and management method using a RFID (radio frequency identification) tag having a LED (light emitting diode), including: transmitting an issuing request signal to the RFID tag through a reader; transmitting data having information about a subject where a corresponding RFID tag is attached to when receiving a response for the issuing request from a RFID tag, requesting the RFID tag to store the transmitted data, and receiving a response thereof; requesting the RFID tag to transmit stored data when a subject having a predetermined condition is requested; determining whether a LED is turned on or off by comparing the predetermined condition with data received from a RFID tag according to the request; and transmitting a request signal to turn on a LED corresponding to the determination result.

According to further another aspect of the invention, the invention provides a method of wireless recognition and management method using a RFID (radio frequency identification) tag having at leas one of LEDs (light emitting diode), including; transmitting an issuing request signal to the RFID tag through a reader; transmitting a sensor reference value related to a condition to managing a subject where a corresponding RFID tag is attached to when a response for the issuing request is received from the RFID tag, requesting the RFID tag to store the transmitted sensor reference value, and receiving a response thereof; and comparing a current sensor value and the stored sensor reference value by the RFID tag when a management subject is required to identify, and transmitting a request signal to turn on a LED.

According to still further another aspect of the invention, the invention provides a method of wireless recognition and management method using a RFID (radio frequency identification) tag having at leas one of LEDs (light emitting diode), including; transmitting an issuing request signal to the RFID tag through a reader; transmitting a sensor reference value related to a condition to manage a subject where a corresponding tag is attached to when a response for the issuing request is received, requesting the RFID tag to store the transmitted sensor reference value, and receiving a response thereof; receiving a sensor reference value and a current sensing value by requesting to the RFID tag when a management subject is required to identify; comparing the received sensor reference value and current sensing value, and determining whether a LED of a corresponding RFID tag is turned on or off; and transmitting a request to a corresponding RFID tag to turn on a LED according to the determination result.

Advantageous Effects

The RFID tag according to the certain embodiments of the present invention allows a user to effectively classify and manages a large quantity of products including medical supplies, blood samples, and agricultural and marine products. Especially, the agricultural and marine products can be systemically managed according to the degree of freshness or according a contamination level thereof. Also, the medical supplies and blood samples can be effectively managed. Furthermore, contaminated blood samples, decomposed medical supplies, and rotten agricultural and marine products can be easily identified using the RFID tags according to the certain embodiments of the present invention.

BRIEF DESCRIPTION OF THE DRAWINGS

The above objects, other features and advantages of the present invention will become more apparent by describing the preferred embodiments thereof with reference to the accompanying drawings, in which.

BEST MODE FOR CARRYING OUT THE INVENTION

Hereinafter, preferred embodiments of the present invention will be described in detail with reference to the attached drawings.

Figure 1:
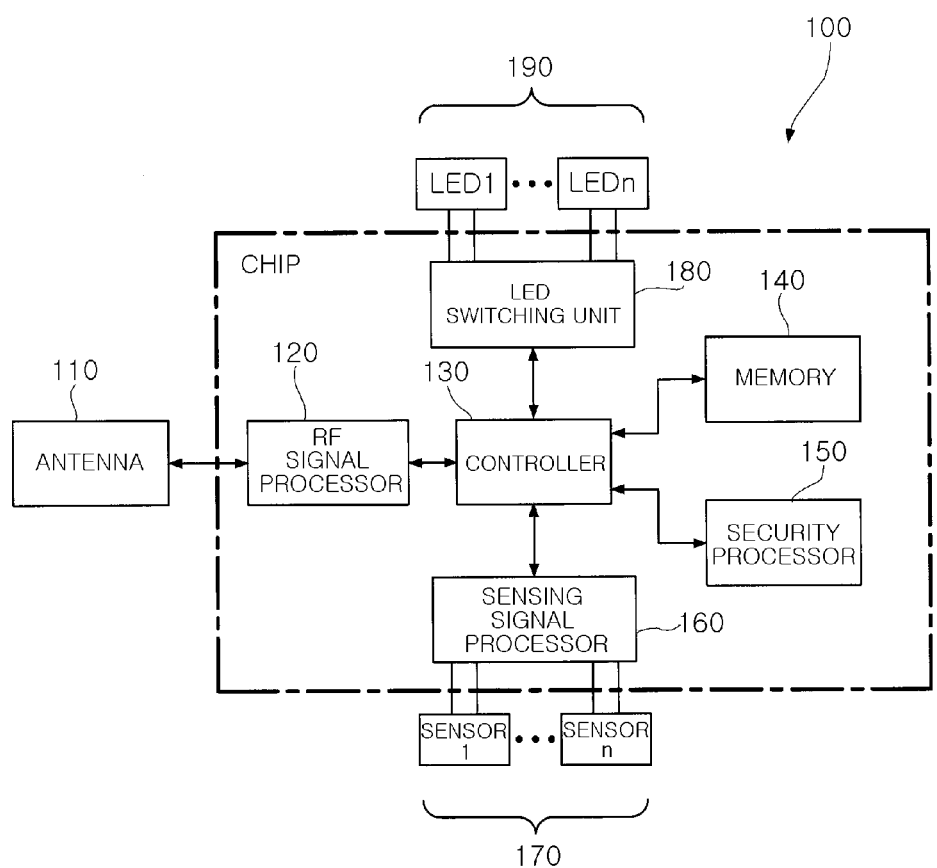
FIG. 1 is a block diagram illustrating a RFID tag according to a first embodiment of the present invention.

FIG. 1 is a block diagram illustrating a RFID tag according to a first embodiment of the present invention.

Referring to FIG. 1, the radio frequency identification (RFID) tag 100 include an antenna 100, a RF signal processor 120, a controller 130, a memory 140, a security processor 150, a sensing signal processor 160, at least one of sensors 170, a LED switching unit 180, and at least one of LEDs 190.

The antenna 110 transmits and receives a wireless signal carrying data transmitted from the RFID tag 100, where the frequency band of the wireless signal is pre-defined.

The RF signal processor 120 demodulates a wireless signal received through the antenna 100 to transmission data, transforms the transmission data to a predetermined wireless signal, and transmits the wireless signal through the antenna 110.

The controller 130 confirms a request of a RFID reader from data inputted from the RF signal processor 120, and generally controls the RFID tag 100 to perform the requested operation. In more specific, the controller 130 analyzes data inputted from the RF signal processor 120. If the input data is a request of storing management information data for subject with a corresponding RFID tag 100 attached, the controller 130 stores the received sensor reference value and data in the memory 140. Afterward, the controller compares a current sensor value and the stored sensor reference value, analyzes the stored data, and controls the LEDs 190 to be turned on/off according to the comparison and analysis result.

The memory 140 stores the sensor reference value and/or management information data in response to the controller 130

The sensor reference value and data, which are stored in the memory 140, may vary according to management subjects.

For example, the sensor reference value or data may be a reference value of a temperature sensor if the management subject is a storage temperature. Also, the sensor reference value or data may be a reference date for calculating a preservation period if the management subject is a preservation period. Furthermore, the sensor reference value or data may be personal information, clinical history, and dosage information of a patient if the management subject is a patient.

The security processor 150 restores received data to original data by decoding received data according to a request of the controller 130 or encodes data to transmit if a predetermined security technology is applied to data. The security processor 150 may be omitted if security technology is not required to a corresponding RFID tag 100

The sensing signal processor 160 transforms a sensing signal outputted from at least one of sensors 170 embedded in the RFID tag 100 to data with a predetermined format processable in the controller 130. After transforming, the sensing signal processor 160 provides the transformed data to the controller 130.

At least one of sensors 170 sense the states of management subjects and peripheral environmental information thereof, which are required to manage management subjects with the RFID tag 100 attached. The types of sensors may vary according to the management subjects. For example, a temperature sensor is used for managing blood, medical supplies, and agricultural and marine products because it requires a storage temperature thereof to be managed. As another example, a biosensor may be used for managing patients to measure bio information of the patients. It is preferable that the sensor 170 outputs a fixed sensing value although the state of the sensing subject varies after the sensing value outputted from the sensor 170 reaches to a predetermined value. In at least one embodiment of the present disclosure, at least one the sensor, if sensing values reach a predetermined sensing value, outputs a fixed sensing value although states of sensing subjects vary and does not function as a sensor.

Figure 3:
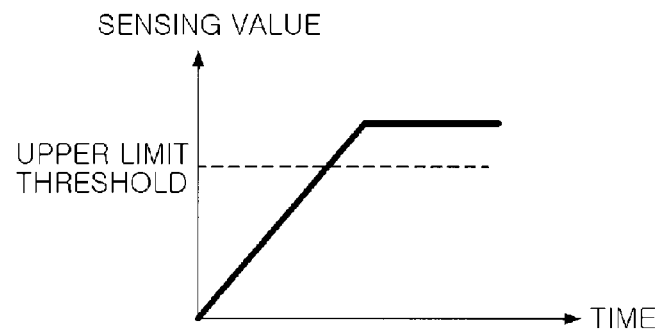
FIGS. 3 (a) and (b) are graphs illustrating the preferable characteristic of a sensor to be applied to a RFID tag according to an embodiment of the present invention.
Figure 3:
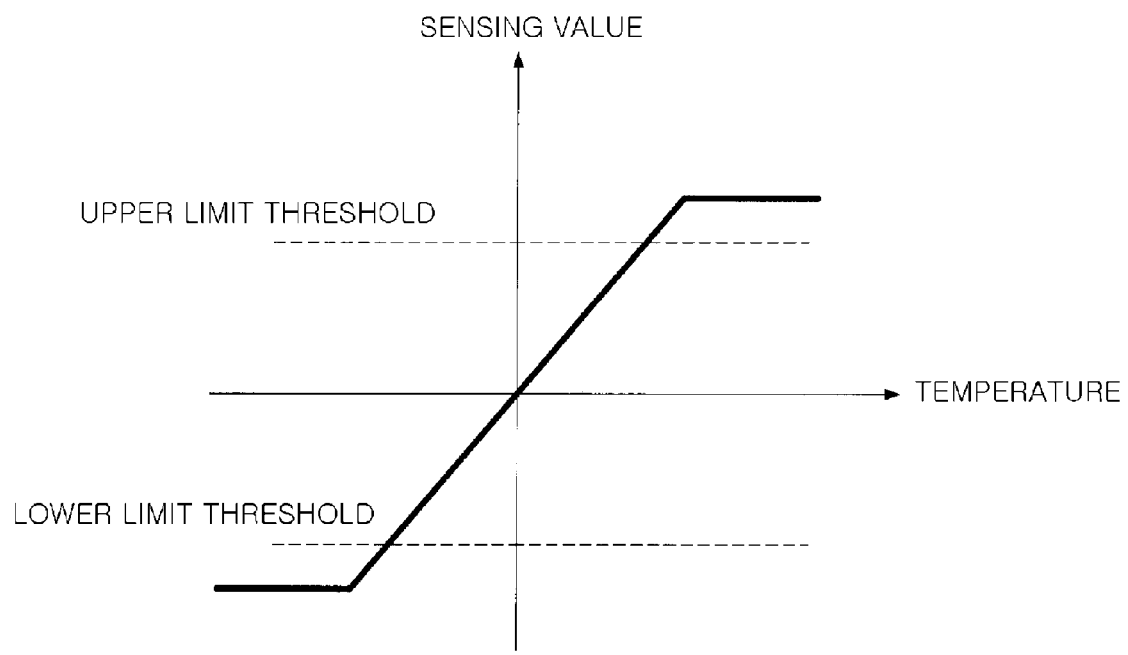

FIGS. 3 (a) and (b) are graphs illustrating the preferable characteristic of a sensor to be applied to a RFID tag according to an embodiment of the present invention. It is preferable that a sensor outputs a fixed sensing value larger than an upper limit threshold from a predetermined time as shown in the graph (a). Or, it is preferable that a sensor outputs a fixed sensing value larger than an upper limit threshold after a temperature increases higher than a predetermined temperature or a fixed sensing value smaller than a lower limit threshold after a temperature decreases lower than a predetermined temperature as shown in the graph (b). For example, if management subjects such as blood, medical supplies, or agricultural and marine products, are exposed at temperature higher or lower than a predetermined storage temperature for a predetermined time, the management subjects are decomposed. If the temperature returns back to the predetermined storage temperature after the management subjects are decomposed, it is difficult for a manager to detect a reason of decomposing the management subjects. In order to detect the reason of decomposition, it is preferable that a sensor has a characteristic to output a fixed sensing value after the sensor reaches a predetermined condition although the sensor operates normally in a normal operation range as shown in FIGS. 3 (a) and (b). As an example of a sensor operated as the described above is a protein composition resistive sensor.

Furthermore, various sensors can be used in the RFID tag according to the present embodiment, for example, a temperature sensor, a pressure sensor, a humidity sensor, a velocity sensor, a sound wave sensor, an optical sensor, and a gas sensor. Also, the sensors 170 can be embodied as a capacitive sensor or a resistive sensor. Furthermore, the sensors 170 can have various electric input signals such as voltage, current, and resistance.

The LED switching unit 180 turns on/off power applied to at least one of LEDs 190 disposed at a corresponding RFID tag 100 in response to control of the controller 130. The LEDs 190 are attached at the corresponding RFID tag 100, are turned on/off in response to the control of the LED switching unit 180 and the controller 130 so as to allow a manager to easily recognize the corresponding RFID tag.

The RF signal processor 120, the controller 130, the memory 140, the security processor 150, the sensing signal processor 160, the LED switching unit 180 can be integrated as one semiconductor chip.

As described above, the RFID tag 100 according to the present embodiment can be used with a wireless recognition technology to manage goods that are easily decomposed, such as blood, medical supplies, and agricultural and marine products. In case of managing the goods that are easily decomposed, the RFID tag 100 stores threshold values for a preservation environment, for example, an upper limit temperature, or a lower limit temperature, and sensor reference values for determining whether the goods are decomposed or not. If the output value of a sensor exceeds the threshold values and the sensor reference values, a LED is turned on so as to let a manager to detect a decomposed good easily. Furthermore, the RFID tag 100 may be used as a reuse-prevention tag. In case of using the RFID tag 100 as the reuse-prevention tag, the controller 130 compares the stored sensor reference value with a current sensing value and prevents a RFID tag from being reused according to the comparison result, thereby enhancing the physical security of the tag.

Using such a RFID tag 100, products are managed in various methods. Such methods for managing products using the RFID tag 100 will be described in later.

Figure 2:
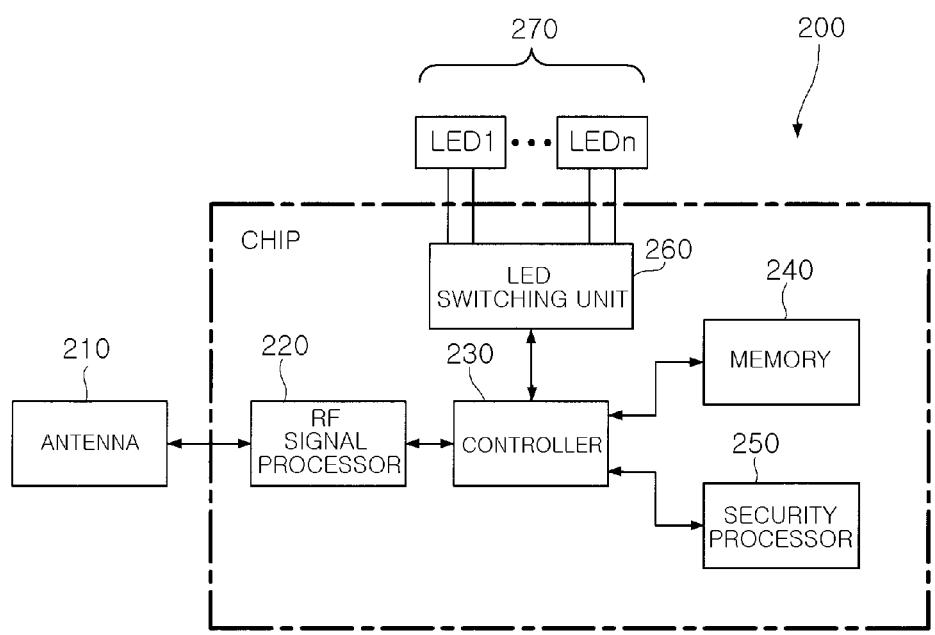
FIG. 2 is a block diagram illustrating a RFID tag according to a second embodiment of the present invention.

FIG. 2 is a block diagram illustrating a RFID tag according to a second embodiment of the present invention.

Referring to FIG. 2, the RFID tag 200 include an antenna 210, a RF signal processor 220, a controller 230, a memory 240, a security processor 250, a LED switching unit 260, and at least one of LEDs 270.

Unlike the RFID tag 100 shown in FIG. 1, the RFID tag 200 does not include a sensor and a sensing signal processor. The antenna 210, the RF signal processor 220, the memory 240, the security processor 250, the LED switching unit 260, and the LED 270 of the RFID tag 200 are similar to those of the RFID tag 100 excepting the controller 230. The controller 230 stores data inputted from the RF signal processor 220 at the memory 240. When a reader requests searching subjects with predetermined conditions, the controller 230 compares the data stored in the memory 230 whether they are satisfied with a corresponding condition or not. If they are satisfied, the LED 270 is turned on.

Such a RFID tag 200 can be applied when a sensor is not required. That is, the RFID tag 200 is used to manage a large quantity of products or a plurality of patients with a wireless recognition technology applied. For example, the RFID tag 200 can be used to manage a plurality of hospitalized patients as follows in a hospital. A RFID tag 200 is attached to each bed of patients by storing clinical history and management information to the RFID tag 200. The LED of the RFID tag is turned on if a corresponding patient is satisfied with a predetermined condition such as a meal time, a medicine time, or an injection time. As another example, the RFID tag 200 can be used to manage products. In this case, the RFID tag 200 stores a producing data of each product and a producing center, and the LED of the RFID tag 200 is turned on/off if the RFID tag 200 is satisfied with a predetermined condition through the reader. Therefore, a manager can easily classify a large quantity of products by a predetermined producing data or producing center. Using such a RFID tag 200, products are managed in various methods. Such methods for managing products using the RFID tag 200 will be described in later.

The LEDs 190 and 270 of the RFID tags 100 and 200 according to the first and second embodiments may be embodied to emit light in various colors such as red, yellow, blue and green. In this case, it is possible to effectively manage products although it requires more complicated management scheme. For example, products can be effectively managed according to decomposition levels, and a large quantity of products can be easily classified using the RFID tag with various color LEDs.

FIG. 4 through FIG. 9 are flowcharts illustrating management methods using a RFID tag according to an embodiment of the present invention. Hereinafter, a wireless recognition and management methods using a RFID tag according to an embodiment of the present invention will be described.

Figure 4:
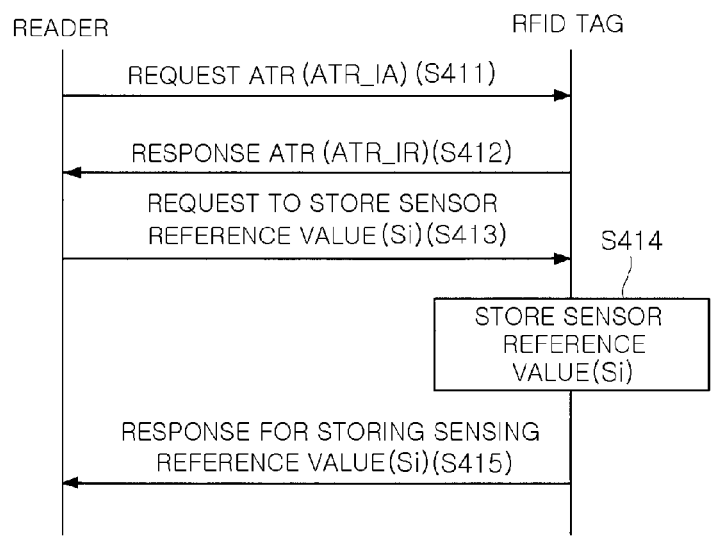
FIG. 4 through FIG. 6 are flowcharts illustrating a wireless recognition and management method using a RFID tag 100 shown in FIG. 1.
Figure 5:
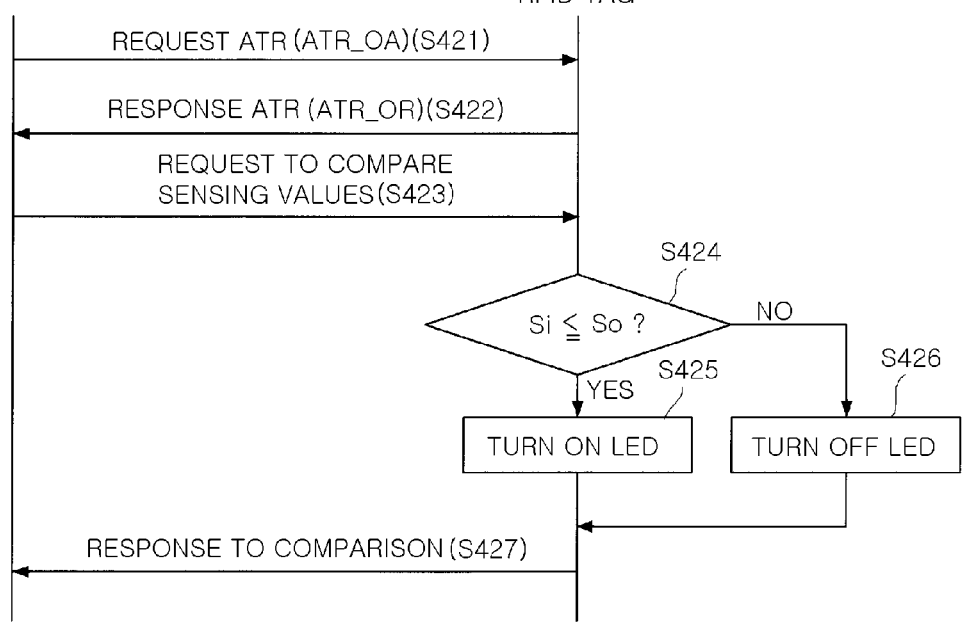
Figure 6:
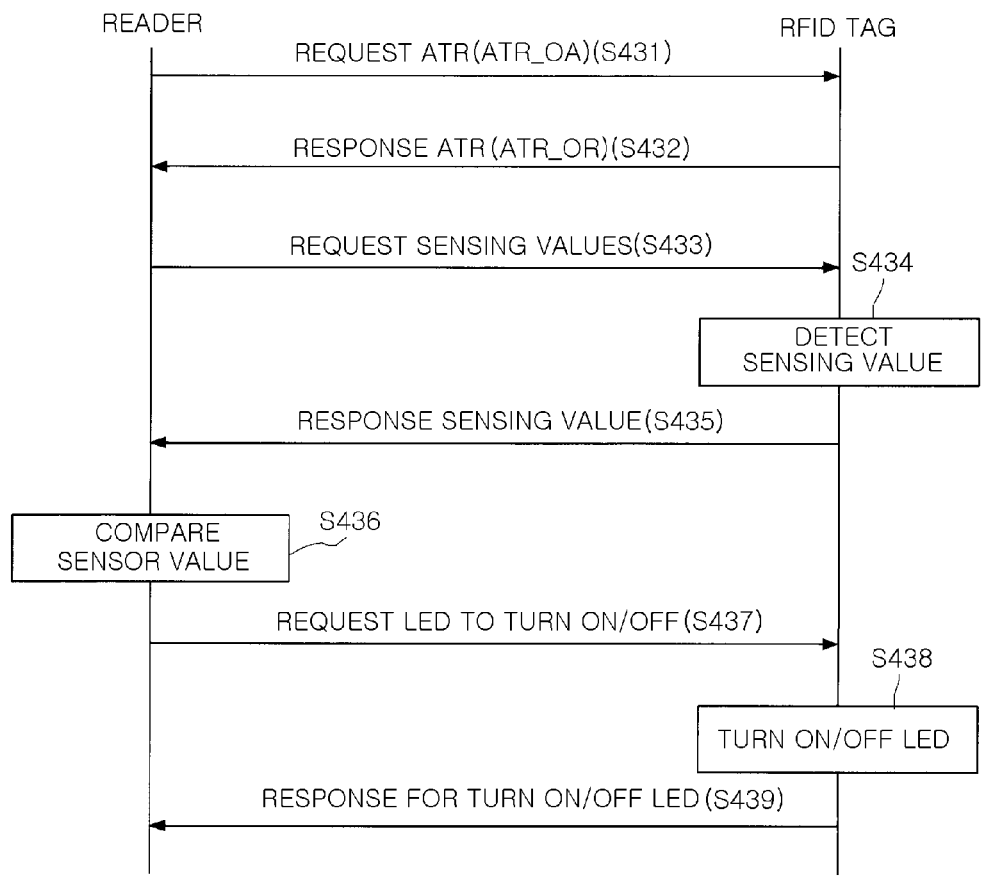

FIG. 4 through FIG. 6 are flowcharts illustrating a wireless recognition and management method using a RFID tag 100 shown in FIG. 1. Specially, FIG. 4 shows a method of issuing a RFID tag, and FIG. 5 and FIG. 6 show a method of driving a RFID tag.

The RFID tag 100 requires an issuing procedure to set basic information into a RFID tag 100 when the RFID tag 100 is newly applied to a wireless recognition and management system. That is, as shown in FIG. 4, when a reader transmits an issuing request signal (ATR_IA) to a corresponding RFID tag 100, the RFID tag 100 in a normal state becomes activated by the issuing request signal and transmits a response signal (ATR_IR) of the request to the reader at steps S411 and S412.

At step S413, the reader requests the RFID tag 100 that successfully responses the issuing request signal (ATR_IA) to store a sensor reference value Si that will be applied to a recognition subject by attaching the RFID tag 100 thereto. Then, the RFID tag 100 receives the request of storing the sensor reference value Si and stores the sensor reference value Si into the memory 140 at step S414. After storing, the RFID tag 100 transmits the response message thereof to the reader at step S415.

The RFID tag 100 can posses a predetermined sensor reference value through the issuing method shown in FIG. 4 before the RFID tag 100 is actually used in a related field such as medical environment, product distribution environment, and a living environment. Herein, the sensor reference value is a digital form of a physical feature sensor value outputted from the sensor 170 in the corresponding RFID tag 100. That is, the physical feature sensor value from the sensor 170 is transformed to an electric signal by the sensing signal processor 160 and the electric signal is transformed to digital values to be processed in the controller 130. After the issuing procedure is finished, the RFID tag 100 is practically applied to various fields such as medical environment, product distribution environment, and living environment. After issuing the RFID tag 100, the RFID tag 100 can be drive like as FIG. 5.

As shown in FIG. 5, a reader transmits a operating request (ATR_OA) to the RFID tag 100, and the RFID tag 100 transmits a response (ATR_OR) for the operating request (ATR_OA) to the reader at steps S421 and S422. A RFID tag 100 in a normal state transmits the response (ATR_OR), but a RFID tag 100 in abnormal state cannot transmit the response. Therefore, if the steps S421 and S422 are successfully performed, the reader requests the RFID tag 100 to compare a current sensor value So with a sensor reference value Si stored in a memory of the RFID tag 100 at step S423. The corresponding RFID tag 100 compares the two values So and Si at step S424. Then, the RFID tag 100 turns on/off the LED 190 according to the comparison result at steps S425 and S426, and the RFID tag 100 transmits a response to the reader to notify of normal operation at step S427. The LEDs 190 are turned on/off according to a control algorithm that is previously defined at the controller. For example, if the current sensor value So is larger than or equal to the sensor reference value Si, the LED 190 is turned on.

In the RFID tag driving method of FIG. 5, the RFID tag makes decision. However, a reader can make decision to drive the RFID tag. FIG. 6 shows a RFID tag driving method with a reader to make decision.

In this case, a reader transmits an operating request (ATR_OA) to a reader, and receives a response thereof from the RFID tag 100 at step S432. When the RFID tag 100 is in a normal state, the reader receives the response from the RFID tag 100. However, if the RFID tag 100 is in an abnormal state, the reader doses not receive the response thereof.

Then, the reader requests sensor values to the RFID tag 100 that transmits the response at step S433. Then, the RFID tag 100 detects a sensor value and transmits the detected sensor value to the reader at steps S434 and S435. The sensor value transmitted from the RFID tag 100 to the reader must include a current sensor value So which is outputted from a sensor 170 of a corresponding RFID tag 100 and transformed at a sensing signal processor 160. Furthermore, the sensor value must further include a sensor reference value Si stored in the memory 140.

After receiving the sensor value, the reader compares the current sensing value So of the RFID tag 100 with the sensor reference value Si, determines on/off state of the LED according to the comparison result, and requests the RFID tag to turn on/off LEDs according to the determination result at steps S436 and S437. The RFID tag 100 turns on/off the LED 190 according to the request, and transmits the result thereof to the reader at steps S438 and S439.

For example, the RFID tag 100 with the described issuing and driving method can be applied to manage medical supplies or blood. That is, RFID tags are attached to each medical supply or blood, and a sensor reference value corresponding to a storage temperature is stored in the RFID tags. Then, a manager instructs the reader to drive the RFID tags based on the driving method. Therefore, a manager can conveniently and effectively select medical supplies and blood which are exposed at higher or lower temperature than the assigned storage temperature.

Unlike the above described embodiments, a reader may include a supplementary memory to store and manage sensor reference values So per each RFID tag. In this case, a RFID tag 100 is not required to additionally manage the sensor reference values. Therefore, the issuing method of FIG. 4 is not required. That is, the reader receives a current sensor value Si from the RFID tag 100 through the driving method shown in FIG. 6, and compares the received current sensor value with the sensor reference values So stored per the RFID tag. According to the comparison result, the reader requests a corresponding RFID tag to turn on/off a LED.

Figure 7:
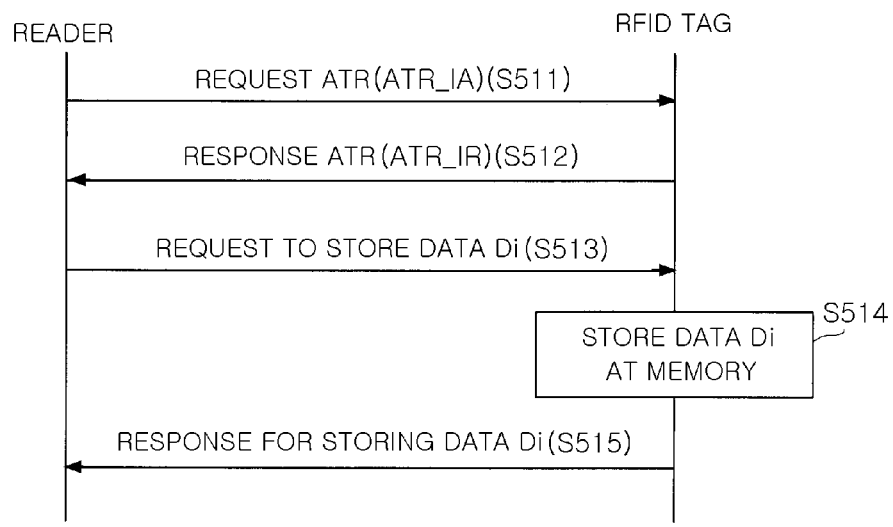
FIG. 7 through FIG. 9 are flowcharts illustrating a wireless recognition and management method using not only a RFID tag 100 but also a RFID tag 200 according to an embodiment of the present invention.
Figure 8:
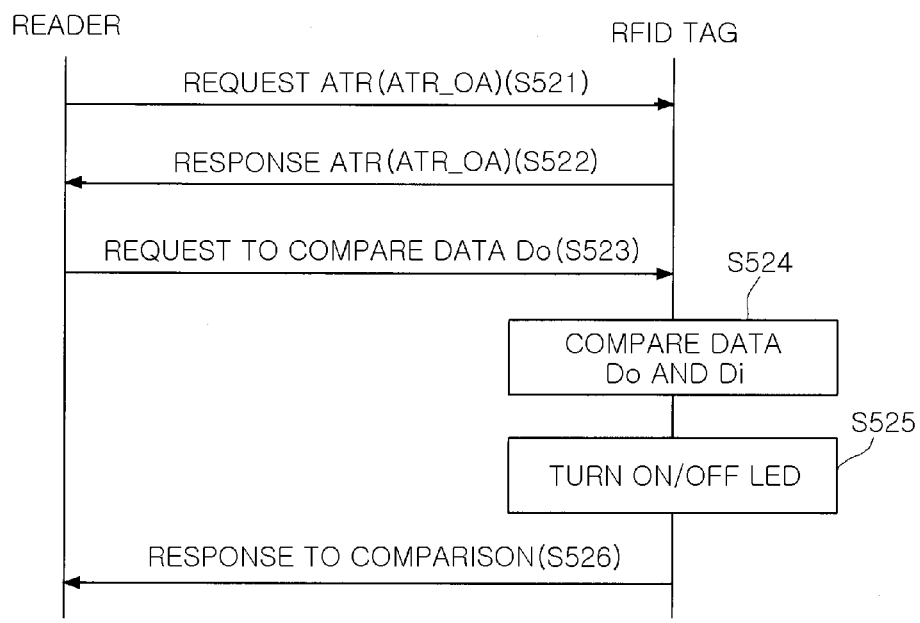
Figure 9:
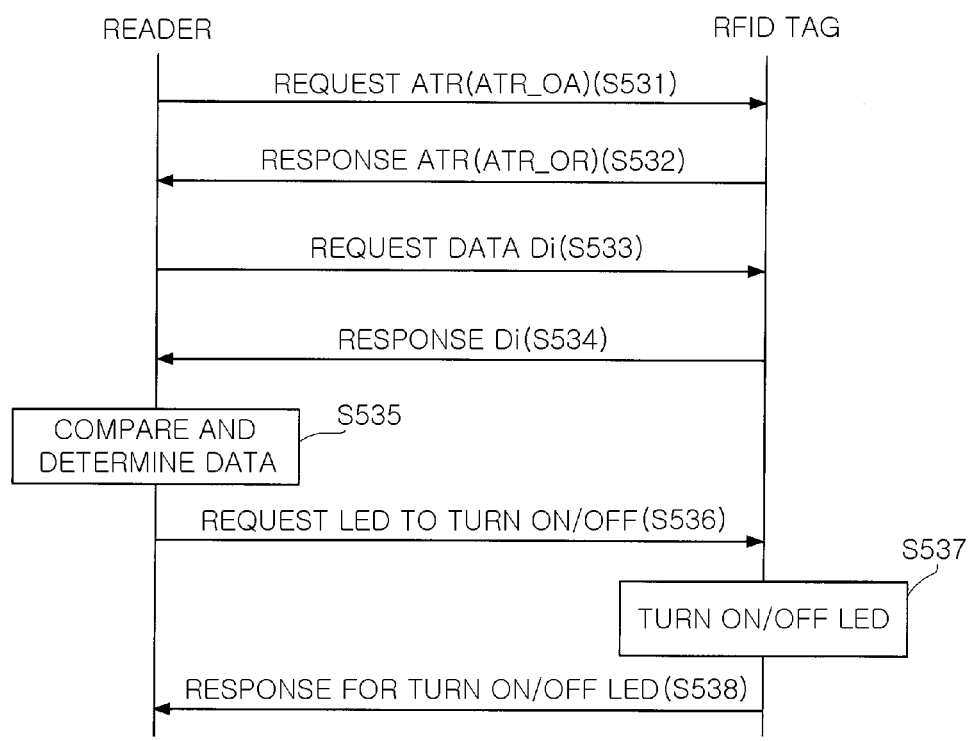

FIG. 7 through FIG. 9 are flowcharts illustrating a wireless recognition and management method using not only a RFID tag 100 but also a RFID tag 200 according to an embodiment of the present invention. In case of using the RFID tag 100, only a sensor function of the RFID tag 100 is not used.

Before practically use the RFID tags 100 and 200 according to the present embodiment to manage subjects, the RFID tags 100 and 200 are required to be issued. For example, patient or medical related data or manufacturing information of products are required to store in the RFID tags 100 and 200.

Referring to FIG. 7, a reader requests an issuing request signal (ATR_IR) to the RFID tags 100 and 200 at step S511. Then, the RFID tags in normal state transmit a response signal (ATR_IR) to the reader at step S512. After successfully performing the steps S511 and S512, the reader transmits data Di having information of management subject, for example, patient or medical related information, to the RFID tags 100 and 200 that receive the response signal, and requests the RFID tags 100 and 200 to store the data Di at step S513. The RFID tags 100 and 200 store the received data in memories 140 and 240 at step S514. Then, the RFID tags 100 and 200 transmit response signals to the reader at step S515.

After finishing the issuing procedure, the corresponding RFID tags 100 and 200 can be used in various fields such as medical environment, living environment, and product distribution environment to identify one that satisfies a desired condition among a plurality of management subjects.

FIG. 8 and FIG. 9 are flowcharts illustrating a method of driving the RFID tags 100 and 200 for wireless recognition and management method according to an embodiment of the present invention.

FIG. 8 shows a driving method based on a RFID tag according to an embodiment of the present invention. After issuing, the RFID tags 100 and 200 receive an operating request signal ATR_OA from the reader at step S521. Then, the RFID tags 100 and 200 transmit the response thereof to the reader at step S522. Afterward, the RFID tag receives a request signal for comparing data from the reader at step S523. Herein, a reference data Do that is a reference for comparison is transmitted with the request signal. The RFID tags 100 and 200 compares the received data Do and the data Di stored in the memories 140 and 240 at step S524, and turns on/off the LEDs 190 and 270 according to the comparison result at step S525. Then, the RFID tags 100 and 200 transmit a response signal to the reader to inform the reader of completion of the comparing request at step S526.

FIG. 9 is a flowchart illustrating a driving method based on a reader according to an embodiment of the present invention. After issuing, the RFID tags 100 and 200 receives a operating request signal from a reader at step S531 and transmits a response thereof to the reader at step S532 to inform the reader that the request is successfully received. Afterward, the RFID tags 100 and 200 receive a request of transferring stored data Di from the reader at step S533. The RFID tags 100 and 200 read the stored data Di from the memories 140 and 240, which was stored through the issuing procedure, and transmit the read data Di to the reader at step S534. The reader compares the received data Di with conditions inputted from a manager and determines whether the LED is turned on or off according to the comparison result at step S535. According to the determination result, the reader transmits the LED on/off request signal to corresponding RFID tags 100 and 200. The RFID tags 100 and 200 turns on/off the LED 190 and 270 according to the received LED on/off request signal at step S537. Then, the RFID tags 100 and 200 transmit a response signal to the reader to inform that the LED on/off request is completed at step S538.

Furthermore, the RFID tags 100 and 200 may include different type of sensors and LEDs to manage products more accurately and efficiently.

For example, the RFID tags 100 and 200 may include a temperature sensor and a humidity sensor for managing medical supplies and blood. The RFID tags 100 and 200 may be controlled to turn on a red LED if the medical supplies or the blood are exposed at high temperature environment, or to turn on a blue LED if they are exposed at high humidity environment. Therefore, a manager can easily detect current states of medical supplies and blood by checking the color of light emitted from the LED, thereby conveniently diagnosing the medical supplies and the blood where they are contaminated or not.

Also, the RFID tags 100 and 200 may include a plurality of LEDs emitting lights in various colors, and may be controlled to emit different color lights according to the control of the controllers 130 and 230. For example, the RFID tags 100 and 200 can be controlled to express a blood sugar level of a patient with diabetes by emitting blue light, red light, and yellow light sequentially so that a doctor can conveniently examines the patient based on the color of LED.

Figure 10:
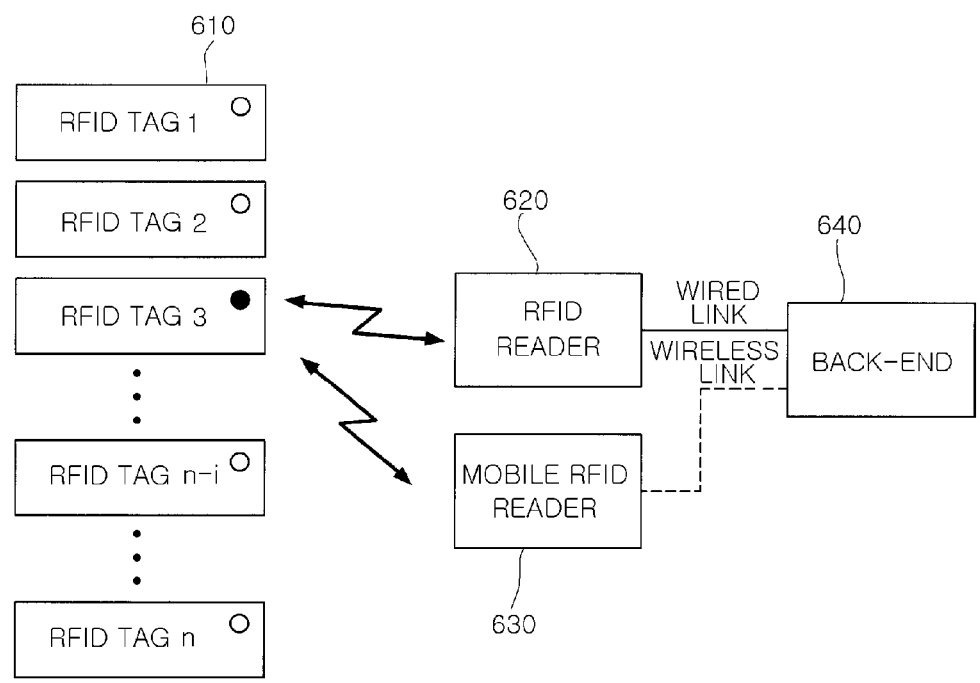
FIG. 10 is a block diagram illustrating a wireless recognition and management system using a RFID tag according to an embodiment of the present invention.

FIG. 10 is a block diagram illustrating a wireless recognition and management system using a RFID tag according to an embodiment of the present invention. The wireless recognition and management system according to the present embodiment includes a plurality of RFID tags 610, a RFID reader 620 and a mobile RFID reader 630 for transmitting and receiving data to/from the plurality of RFID tags 610, and a back-end device 640 for controlling the plurality of RFID tags 610 through the RFID reader 620 and the mobile RFID reader 630.

Each of the plurality of RFID tags 610 has a structure shown in FIG. 1 and/or FIG. 2, and they are attached to management subjects such as a plurality of medical supplies and blood.

The RFID reader 620 is connected to the back-end device 640 through a wired link and is connected to the plurality of RFID tags 610 through a wireless link. The RFID reader 620 needs to be located within a data transmittable range from the plurality of RFID tags 610.

The mobile RFID reader 630 is connected to the back-end device 640 through a wireless link and connected to the plurality of RFID tags 610 through a wireless link.

Since a distance for transmitting and receiving data between the plurality of RFID tags 610 and the readers 630 and 640 is limited, the RFID reader 620 is connected to the back-end device 640 through the wired link. Therefore, the RFID reader 640 has a narrow usable range. That is, it is difficult to carry the RFID reader 640 around. However, the mobile RFID reader 630 can be conveniently carried and has a wide usable range because it is connected to the back-end device 640 through the wireless link.

The back-end device 640 controls the plurality of RFID tags 610 through the readers 620 and 630. The back-end device 640 includes a central controlling function and a user interface function. Furthermore, the back-end device 640 includes management programs according to an application field thereof.

A manager performs the issuing method by driving the readers 620 and 630 to store each sensor reference value or management information into each of the RFID tags 610. Afterward, if a request of identifying a predetermined subject is received, the driving method is performed through the readers 620 and 630. After performing the driving method, the RFID tags satisfied by the identifying condition turn on LEDs to inform the manager of the location thereof.

Hereinafter, the operation of the wireless recognition and management system according to the present embodiment will be briefly described using a case of managing blood samples as an example. As the first step, basic data of patients are inputted and stored in corresponding RFID tags 610. The basic data include a name, an age, a sex, a data of taking a blood sample, and a first test. Then, the RFID tags are attached to each of sample containers. Herein, the RFID tags 610 may be attached the sample containers before inputting and storing the basic information into the tags As the second step, after putting the blood sample of a predetermined patient into the sample container, a manager requests a corresponding RFID tag 610 to examine the blood sample using the readers 630 and 640. Then, the RFID tag 610 senses the information about the blood sample and/or peripheral environment using sensors. Herein, if the blood sample has a predetermined value, the RFID tag 610 emits yellow light using a related LED. Therefore, a user can effectively read information of blood samples of a plurality of patients.

As the third step, when the blood sample is dumped after fining examining of the blood sample, the information stored in the RFID tag 610 is removed in order to reuse the RFID tag 610. When the blood sample is continuously stored or managed, information for identifying a corresponding sample and for managing the same are stored in the tag 610.

Such information of the REID tag 610 can be transmitted to the back-end device 61 through the readers 620 and 630, and the information can be used for providing various services.

Figure 11:
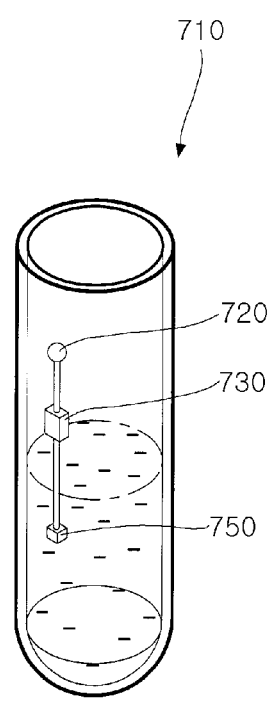
FIG. 11 and FIG. 12 show examples of a RFID tag according to the present invention.
Figure 12:
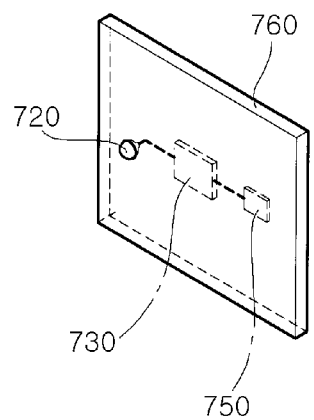

FIG. 11 and FIG. 12 show examples of a RFID tag according to the present invention. As shown in FIG. 11, a RFID tag according to the present embodiment can be embedded in a container such as a urine container, a blood container, and a cylinder. Also, the RFID tag according to the present embodiment can be embedded to easily attach to any subject by being packaged with vinyl, paper, or plastic and including an adhesive member or an attaching unit as shown in FIG. 12.

The RFID tag can be embodied in various forms.

Although the preferred embodiments of the present invention have been disclosed for illustrative purpose, those skilled in the art will appreciate that various modifications, additions and substitutions can be made without departing from the scope and spirit of the invention as defined in the accompanying claims.

The invention claimed is:

1. A method of wireless recognition and management using a radio frequency identification (RFID) tag having at least one light emitting diode (LED) and at least one sensor, the method comprising:
transmitting an issuing request signal to the RFID tag through a reader;
transmitting a sensor reference value related to a condition for managing a management subject to which the RFID tag is attached when a response to the issuing request signal is received from the RFID tag, requesting the RFID tag to store the transmitted sensor reference value, and receiving a response thereof;
determining a current sensor value corresponding to the stored sensor reference value; and
transmitting a request signal to compare the current sensor value and the stored sensor reference value and turning on the at least one LED by the RFID tag when the management subject is required to be identified and based on the determination result,
wherein the at least one sensor outputs a fixed sensing value and stops functioning as a sensor if a sensing signal of the at least one sensor reaches a predetermined threshold.

2. A method of wireless recognition and management using a radio frequency identification (RFID) tag having at least one light emitting diode (LED) and at least one sensor, the method comprising;
transmitting an issuing request signal to the RFID tag through a reader;
transmitting a sensor reference value related to a condition to manage a management subject to which the RFID tag is attached when a response to the issuing request signal is received, requesting the RFID tag to store the transmitted sensor reference value, and receiving a response thereof;
receiving the sensor reference value and determining a current sensing value corresponding to the received sensor reference value by a request to the RFID tag when the management subject is required to be identified;
comparing the received sensor reference value and the current sensing value, and determining whether the at least one LED of the RFID tag is turned on or off; and
transmitting a request to the RFID tag to turn on the at least one LED according to the determination result,
wherein the at least one sensor outputs a fixed sensing value and stops functioning as a sensor if a sensing signal of the at least one sensor reaches a predetermined threshold.

3. The method according to claim 1, wherein the at least one sensor detects states of the management object and a peripheral environment of the sensing object, and the at least one LED emits light in different colors based on the detected states of the management subject and peripheral environment.

4. The method according to claim 2, wherein the at least one sensor detects states of the management object and a peripheral environment of the sensing object, and the at least one LED emits light in different colors based on the detected states of the management subject and peripheral environment.

\* \* \* \* \*